(12) United States Patent
Marmarelis (10) Patent No.: US 7,094,205 B2
(45) Date of Patent: Aug. 22, 2006

(54) HIGH-RESOLUTION 3D ULTRASONIC TRANSMISSION IMAGING

(75) Inventor: Vasilis Z. Marmarelis, Irvine, CA (US)

(73) Assignee: Alfred E. Mann Institute for Biomedical Engineering at the University of Southern California, Los Angeles, CA (US)

(*) Notice: Subject to any disclaimer, the term of this patent is extended or adjusted under 35 U.S.C. 154(b) by 7 days.

(21) Appl. No.: 10/117,763

(22) Filed: Apr. 5, 2002

(65) Prior Publication Data

US 2003/0069501 A1 Apr. 10, 2003

Related U.S. Application Data

(60) Provisional application No. 60/282,001, filed on Apr. 6, 2001.

(51) Int. Cl.
*A61B 8/02* (2006.01)

(52) U.S. Cl. ....................................................... 600/448
(58) Field of Classification Search ................ 600/440, 600/441, 443, 447, 448; 73/602; 128/915–916
See application file for complete search history.

(56) References Cited

U.S. PATENT DOCUMENTS

| | | | |
|---|---|---|---|
| 4,075,883 A | | 2/1978 | Glover |
| 4,105,018 A | | 8/1978 | Greenleaf et al. |
| 4,137,777 A | * | 2/1979 | Haverl et al. .................. 73/620 |
| 4,252,025 A | | 2/1981 | Robinson |
| 4,279,157 A | * | 7/1981 | Schomberg et al. ........... 73/618 |
| 4,317,369 A | | 3/1982 | Johnson |
| 4,325,258 A | | 4/1982 | Foster |
| 4,478,083 A | | 10/1984 | Hassler et al. |
| 4,478,084 A | | 10/1984 | Hassler et al. |
| 4,509,368 A | * | 4/1985 | Whiting et al. ................ 73/624 |
| 4,541,436 A | | 9/1985 | Hassler et al. |
| 4,589,284 A | | 5/1986 | Breimesser et al. |
| 5,014,712 A | * | 5/1991 | O'Donnell .................... 600/447 |
| 5,311,095 A | * | 5/1994 | Smith et al. .................. 310/334 |
| 5,318,028 A | | 6/1994 | Mitchell et al. |
| 5,433,202 A | | 7/1995 | Mitchell et al. |
| 5,640,960 A | | 6/1997 | Jones et al. |
| 6,122,542 A | * | 9/2000 | Lee et al. ...................... 600/427 |
| 6,161,034 A | * | 12/2000 | Burbank et al. .............. 600/431 |
| 6,385,474 B1 | * | 5/2002 | Rather et al. ................. 600/407 |
| 6,475,150 B1 | * | 11/2002 | Haddad ......................... 600/448 |
| 2002/0186893 A1 | | 12/2002 | Marmarelis |

FOREIGN PATENT DOCUMENTS

| | | |
|---|---|---|
| EP | 1046929 A2 | 10/2000 |
| EP | 02763998 | 10/2005 |
| WO | WO 95 29737 A1 | 11/1995 |
| WO | WO 97 29699 A1 | 8/1997 |

* cited by examiner

*Primary Examiner*—Francis J. Jaworski
(74) *Attorney, Agent, or Firm*—McDermott Will & Emery LLP (57) ABSTRACT

A system for providing high resolution imaging of objects having sub-millimeter dimensions comprised of at least one transmitter, at least one receiver, a coupling chamber, and a processor for recording attenuation and time of flight profiles of the transmitted signals. The signals are conditioned in a manner to provide high signal-to-noise ration (SNR) and minimal crosstalk and multipath effects at the receiver.

30 Claims, 6 Drawing Sheets

FIG. 10 ary of the invention

HIGH-RESOLUTION 3D ULTRASONIC TRANSMISSION IMAGING

RELATED APPLICATIONS

The present application claims priority to provisional application Ser. No. 60/282,001, filed Apr. 6, 2001, the contents of which are hereby incorporated by reference in their entirety.

BACKGROUND OF THE INVENTION

1. Field of the Invention

This invention relates to imaging a three dimensional object using high resolution scanning in tomographical applications.

Specifically, the present invention relates to signal processing systems and methods for creating a high-resolution image of an object using ultrasonic tomography.

2. General Background

Ultrasonic transmission tomography has been used in the past for two dimensional imaging of an object of interest. The signals used for transmission were either pulse or sinusoidal waveforms.

There are often several limitations in this prior art, such as: (i) the resolution of the image of the object is limited, (ii) the time for scanning an object of interest may be quite long, and (iii) there are errors due to cross talk or multipath effects when multiple transmitter elements are used for simultaneously transmitting signals.

Also, the systems used in 3D imaging involve reflection mode (pulse echo) as a means for communicating a signal between a transmitter and a receiver. As is well known, in pulse-echo mode of communication, the receiver element operates on a signal bounced off an object. No comparable imaging systems are known for transmission mode where the receiver element can operate on a signal attenuated and diffracted about an object.

SUMMARY OF THE INVENTION

The present invention rapidly creates a high resolution 3D image by scanning an object using at least one transmitter and at least one receiver. When there are multiple transmitter and receiver elements, there is minimal crosstalk between signals, and a high signal to noise ratio (SNR) at the receiver.

Applications of the subject invention are vast and include ultrasonic computed tomography for medical applications and industrial applications of non-destructive evaluation.

One embodiment of the present invention is a system for creating an image of an object comprising: (i) at least one transmitter that transmits a signal; (ii) at least one receiver positioned to receive the signal; (iii) an area between the transmitter and the receiver for receiving the object in a position that causes at least portions of the signal to scatter before the signal is received by the receiver; and (iv) a processor in communication with the receiver for extracting an attenuation profile and a time of flight profile from the signal and for creating an image of the object based on these profiles. The system may include apparatus that causes the transmitter and the receiver to be fixed in position relative to one another and that causes the transmitter and the receiver to move relative to the object in at least two different directions. In one embodiment, the transmitter and/or receiver includes a transducer that has at least one linear dimension less than one millimeter. The transmitter and the receiver operate in transmission mode, unlike typical reflection mode (pulse-echo) systems.

Another embodiment of the present invention is a system for creating an image of an object comprising: (i) at least one transmitter that transmits a signal; (ii) at least one receiver positioned to receive the signal; (iii) an area between the transmitter and the receiver for receiving the object in a position that causes at least portions of the signal to be scattered before the signal is received by the receiver; and (iv) a processor in communication with the receiver for creating a discernable image of the object having dimension of less than one millimeter. In one embodiment, the at least one transmitter is excited by a bipolar signal, and the signal transmitted by the at least one transmitter is an ultrasonic signal. In another embodiment, the transmitted signal is of a frequency greater than 15 MHz that is above the frequency range used in medical ultrasonic imaging. This ensures higher imaging resolution, in spite of the higher attenuation associated with propagation of higher frequencies. In a still further embodiment, the transducer in the transmitter/receiver has all linear dimensions less than one millimeter.

Another embodiment of the present invention is a system for creating an image of an object comprising: (i) a plurality of transmitters, each transmitter transmitting a signal that is substantially orthogonal to the signal transmitted by the other transmitters; (ii) a plurality of receivers, each positioned to receive the substantially orthogonal signals from the transmitters and each including a correlator that extracts at least one of the orthogonal signals received by said receiver; (iii) an area between said transmitters and said receivers for receiving the object in a position that causes at least portions of at least one of the orthogonal signals to be scattered before it is received; and (iv) a signal processor in communication with the receivers for extracting attenuation profiles and time of flight profiles from the signals and for creating an image of the object based on these profiles. In one embodiment each of the substantially orthogonal signals is a binary sequency of 64 bit length.

A still further embodiment of the present invention is a system for creating an image of an object comprising: (i) a plurality of transmitters, each transmitting a signal; (ii) a plurality of receivers, each positioned to receive the signals; (iii) an area between said transmitters and said receivers for receiving the object in a position that causes at least portions of at least one of the signals to scatter before that signal is received by at least one of said receivers; and (iv) a processor in communication with said receivers for creating an image of the object. In one embodiment, the plurality of transmitters and/or the plurality of receivers are spaced apart from one another by less than one millimeter.

A still further embodiment of the present invention is a system for creating an image of an object that is fixed relative to a frame of reference comprising: (i) at least one transmitter that transmits a signal; (ii) at least one receiver positioned to receive the signal; (iii) an area between the transmitter and the receiver for receiving the object in a position that causes at least portions of the signal to be scattered before it is received by the receiver; and (iv) a processor in communication with the receiver for creating an image of the object and for generating at least one coordinate of the object relative to a frame of reference. In one embodiment, the object is substantially fixed relative to a surface that substantially surrounds the object. In one embodiment, the frame of reference includes an indicia associated with the surface. In one embodiment, the indicia is one or more pieces of tape or wires affixed to the surface.

In another embodiment of the present invention, a system for creating an image of an object comprises, (i) an array of transmitters, each transmitter transmitting a signal, (ii) an array of receivers, each receiver positioned to decouple one of the transmitted signals, (iii) an area between the transmitter and the receiver for receiving the object in a position that causes at least portions of at least one of the signals to be scattered before it is received by the receiver, (iv) a processor in communication with the receiver for extracting attenuation profiles and time of flight profiles from the signals and for creating an image of the object based on these profiles. Each of the receivers decouples the one of the transmitted signals using either code division, time division, or frequency division, or any combinations thereof. Furthermore, the array of transmitters/receivers may be one dimensional, two dimensional, or three dimensional.

BRIEF DESCRIPTION OF THE DRAWINGS

In order that the manner in which the above-recited advantages and objects of the invention are attained, as well as others which will become apparent, more particular description of the invention briefly summarized above may be had by reference to the specific embodiments thereof that are illustrated in the appended drawings. It is to be understood, however, that the appended drawings illustrate only typical embodiments of the invention and are therefore not to be considered limiting of its scope, for the invention may admit to other equally effective embodiments.

DETAILED DESCRIPTION OF ILLUSTRATIVE EMBODIMENTS OF THE INVENTION

Figure 1:
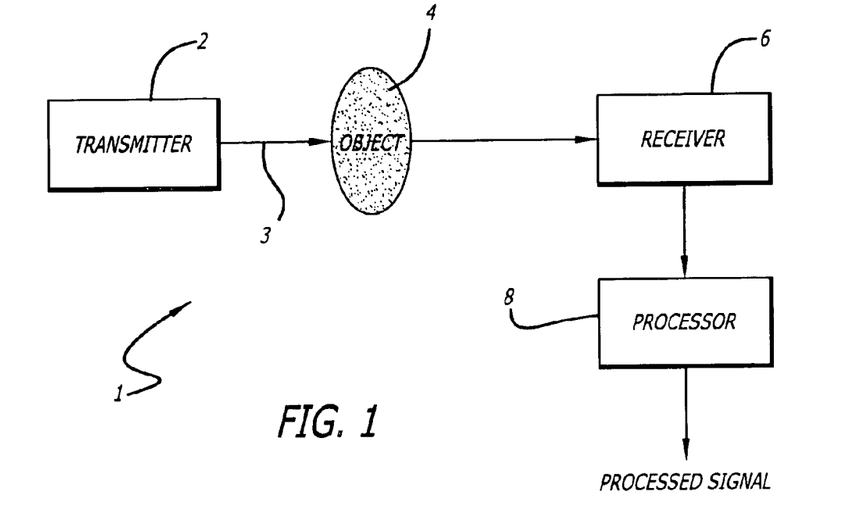
FIG. 1 is a general overview of one embodiment of a system incorporating the present invention for creating a high resolution image of an object. The system includes one transmitter, one receiver, and a processor for generating a high resolution output.

The general overview of one embodiment of a system 1 incorporating the present invention for creating a high resolution image of an object is shown in FIG. 1. The system includes a transmitter 2 used for transmitting a signal 3, a receiver 4, which may include a piezoelectric transducer, positioned to receive the signal, an area between the transmitter and the receiver for receiving an object 4, and a processor 8 for generating a high resolution output signal. This output signal could be either an analog/digital signal or an image. The object 4 is shown in a position that causes at least portions of the signal 3 to be scattered before it is received by the receiver 6. In one embodiment, the object has at least one dimension less than one millimeter. In one embodiment, the object is a lesion that is to be detected in tomographical applications. The transmitter 2 in one embodiment includes a simple piezoelectric transducer that is excited by a bipolar signal having two levels (e.g., +1 and −1) and transmits a pulse signal towards the receiver 6. In one embodiment, the transmitted signal has a center frequency between 1 MHz and 15 MHz. In another embodiment, the transmitted signal has a center frequency greater than 15 MHz. In an exemplary embodiment the transmitted signal is an ultrasonic signal. The output from the receiver 6 is passed to the processor 8. The processor 8 extracts attenuation profiles and a time of flight profile from the signal and for creating an image of the object based on these profiles (as will be explained later).

Figure 2:
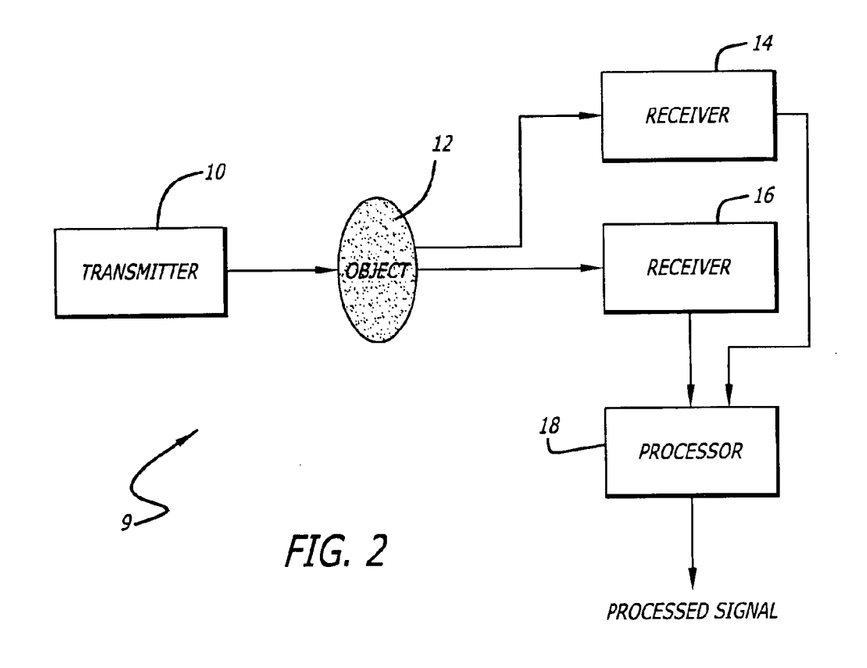
FIG. 2 is a general overview of another embodiment of a system incorporating the present invention for creating a high resolution image of an object. The system includes one transmitter, a plurality of receivers, and a processor for generating a high resolution output.

In another illustrative embodiment, a system 9 incorporating the present invention for creating a high resolution image of an object is shown in FIG. 2. The system includes a transmitter 10 transmitting a signal, multiple receivers 14 and 16 positioned to receive the signal, an area between the transmitter and the receiver for receiving an object 12, and a processor 18 for generating a high resolution output signal. While only two receivers 14 and 16 are shown, it is to be understood that there can be more than two receivers. The object 4 is shown in a position that causes at least portions of the signal to be scattered before it is received by the receivers 14 and 16. The outputs from the receivers are passed to a processor 18. The processor 18 extracts attenuation profiles and a time of flight profile from the signal and for creating an image of the object based on these profiles (as will be explained later). The receivers 14 and 16 may also include simple piezoelectric transducers (elements) and according to one embodiment may be spaced less than a millimeter apart, thus providing sub-millimeter azimuth resolution.

Figure 3:
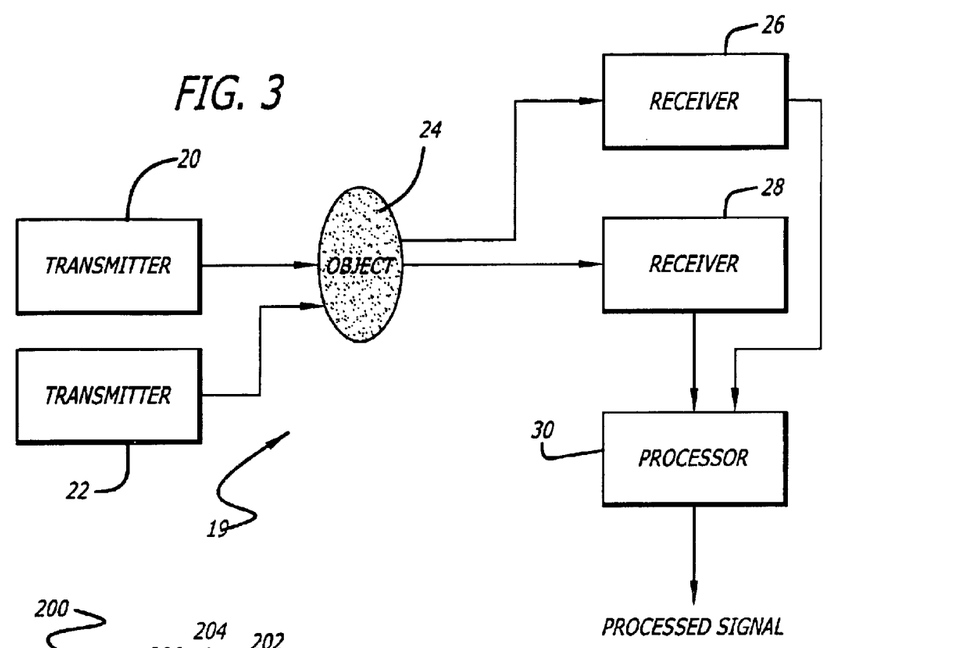
FIG. 3 is a general overview of another embodiment of a system according to the present invention for creating a high resolution image of an object. The system includes a plurality of transmitters, a plurality of receivers, and a processor for generating a high resolution output.

In yet another illustrative embodiment, a system 19 incorporating the present invention for creating a high resolution image of an object is shown in FIG. 3. The system includes multiple transmitters 20 and 22 for transmitting multiple signals, multiple receivers 26 and 28, positioned to receive the multiple signals, an area between the transmitters and the receivers for receiving an object 24, and a processor 30 for generating a high resolution output signal. While only two transmitters 20 and 22 and two receivers 26 and 28 are shown, it is to be understood that there can be more than two transmitters and more than two receivers. The object 24 is shown in a position that causes at least portions of the signals to be scattered before it is received by the receivers 26 and 28. The output from the receivers are passed to a processor 30. The processor 30 extracts attenuation profiles and time of flight profiles from the signals and for creating an image of the object based on these profiles (as will be explained later).

In one embodiment, the multiple signals that are transmitted by the transmitters 20 and 22 may be substantially orthogonally coded so as to achieve a high signal-to-noise ratio (SNR) and, at the same time, minimize cross-talk and multipath effects at the receivers 26 and 28. Orthogonal coding of signals is well known to a person skilled in the art (for example, Gram-Schmidt orthogonalization process may be used to develop orthogonally coded signals). However, orthogonality must be retained also over several correlation lags. Also, it is to be noted that due to the imprecision in computations, the signals may not be perfectly orthogonal but may rather be approximately or substantially orthogonal. In one embodiment, the length of each of the substantially orthogonally coded signals is of 64 bits. The transmitter and receiver elements may be arranged in an array. In one aspect, the array may be linear or one dimensional. Alternatively, the array geometry could also be two or three dimensional.

Figure 4:
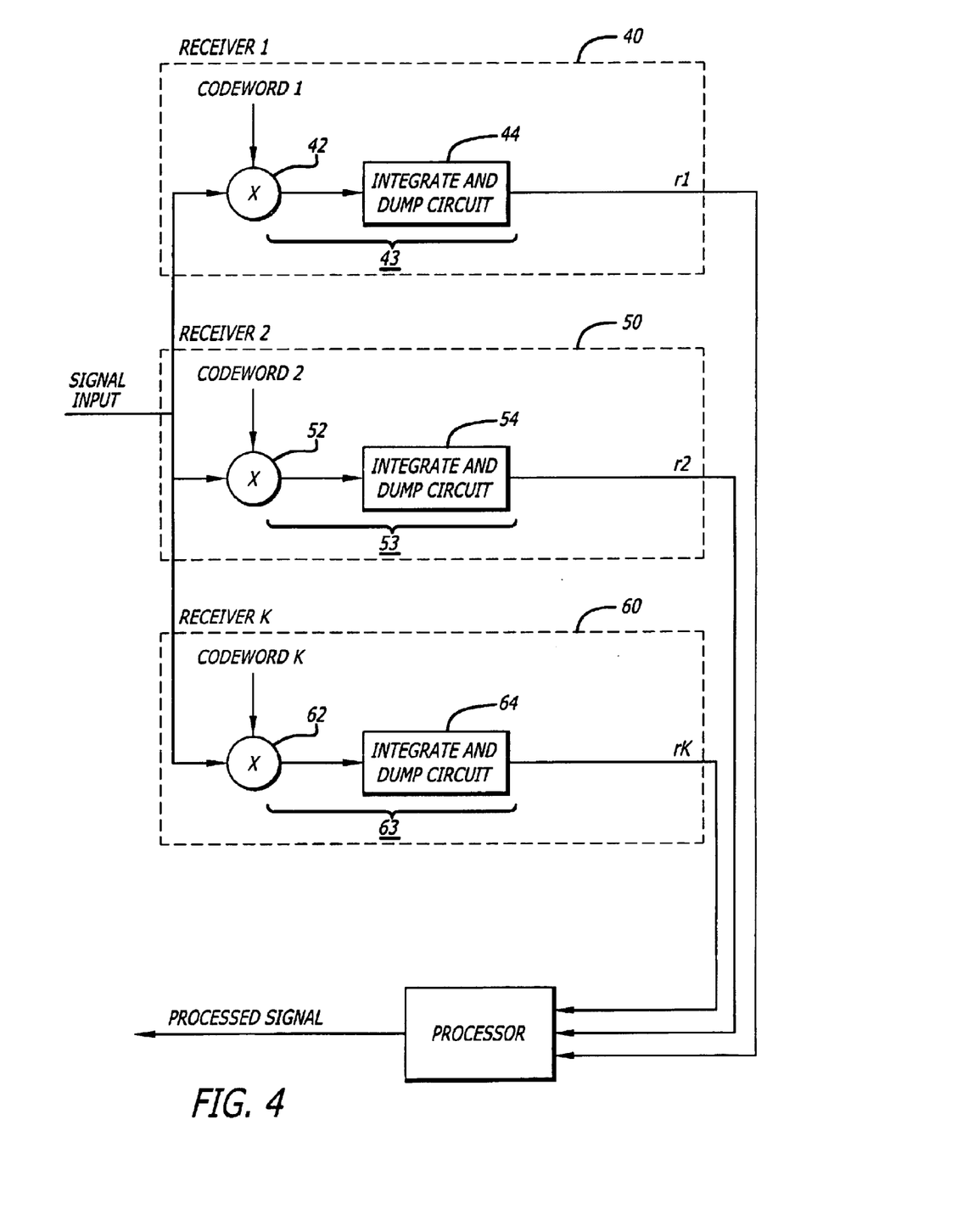
FIG. 4 shows one embodiment, according to the present invention, of the receivers in FIG. 3 for decoupling only one of the transmitted signals.

FIG. 4 shows one embodiment, according to the present invention, of the receivers in FIG. 3 for decoupling one of the transmitted signals. Each of the receivers 40, 50, and 60 are positioned to receive the substantially orthogonal signals in digitized form from the multiple transmitters. Each of the receivers 40, 50, and 60, includes a correlator 42, 52, and 62 and integrators 44, 54, 64 respectively for extracting one of the substantially orthogonal signals received by the corresponding receiver. The outputs are supplied to a processor 70 for extracting attenuation profiles and time of flight profiles from the discrete signals and for creating an image of the object based on these profiles (as will be explained later).

Figure 5:
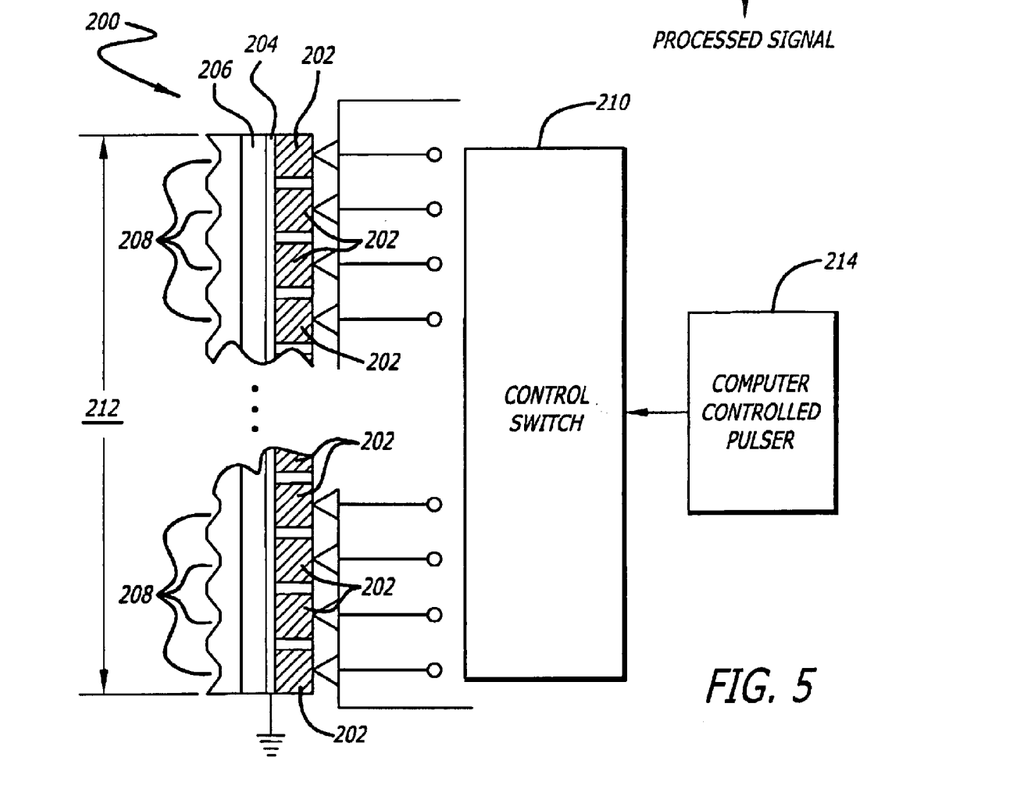
FIG. 5 shows one embodiment, according to the present invention, of components associated with multiple transmitter elements.

FIG. 5 shows one embodiment, according to the present invention, of the components associated with multiple transmitter elements. A computer controlled pulser 214 applies bipolar or monopolar excitation signals through a control switch 210 to each transmitting element (transducer) 202 in a group of multiple transmitting elements labeled as an array 212. In one embodiment, the control switch 210 applies simultaneous excitation to all or a subset of these transducers. Alternatively, the switch 210 can be programmed to apply non-simultaneous excitation to the transmitting elements. This may be achieved by having simple delay circuits, in the switch 210, that delay each signal by an appropriate amount. The transmitted signals from the multiple transmitting elements may be ultrasonic with a frequency greater than 15 MHz. The signals transmitted by the transmitting elements may be substantially orthogonally coded to obtain the advantages discussed above. A common electrode 204 provides grounding to the transmitting elements. An acoustic coupling or matching layer 206 is provided to maximize the energy output from the transmitting elements 202. Acoustic lenses 208 may be used to better focus the signals transmitted by the transmitting elements.

Figure 6:
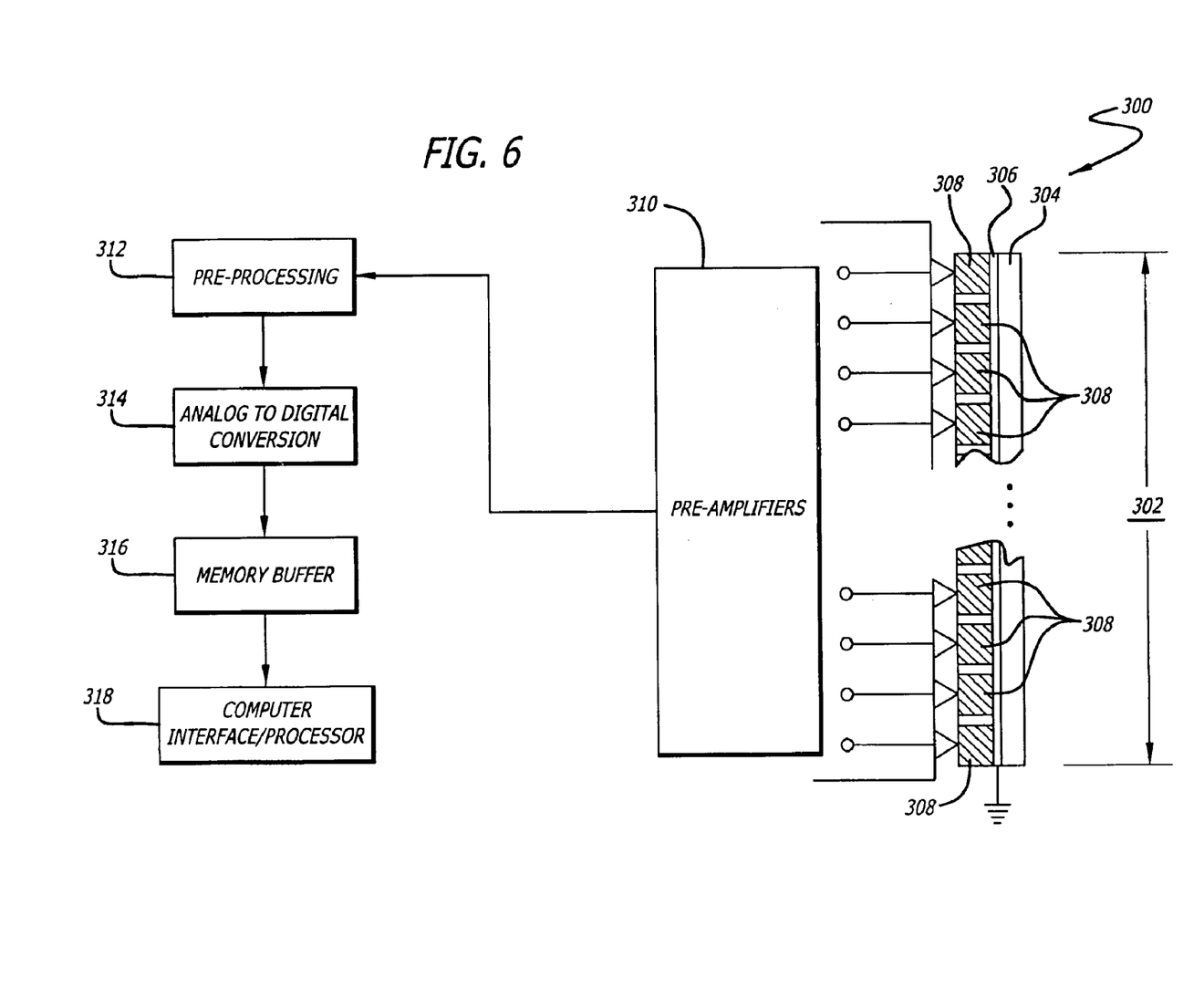
FIG. 6 shows one embodiment, according to the present invention, of components associated with multiple receiver elements.

FIG. 6 shows one embodiment, according to the present invention, of components associated with multiple receiver elements. Receiving elements 308 in an array of receiving elements depicted by 302, are used for receiving the transmitted signals. Reference numerals 304 and 306 indicate a matching layer and common electrode respectively and generally provide the same functionality of the matching layer and common electrode as described in relation to FIG. 5, above. A bank of pre-amplifiers 310 is used to compensate for any attenuation of the transmitted signals by means of amplification. The output from the bank of pre-amplifiers 310 is applied to a pre-processing system 312 that performs band-pass filtering and signal conditioning. The output from the pre-processing system 312 is applied to an analog to digital (A/D) conversion system 314 that provides a digital/discrete output. The output of the A/D converter is transferred to a memory buffer 316 for processing through a computer interface/processor 318. In one embodiment, the processing at 318 includes the same operation of the correlator-integrator structure 43, 53, and 63 in FIG. 4.

Figure 7:
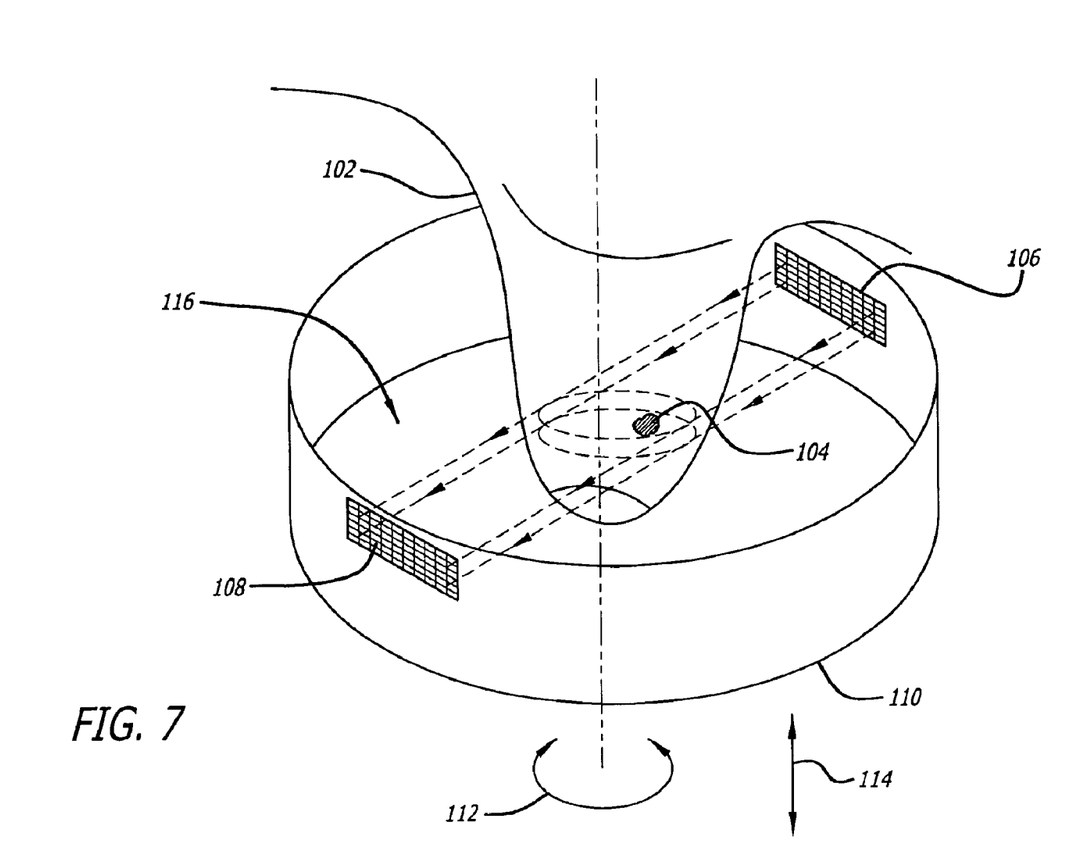
FIG. 7 shows one embodiment, according to the present invention, of a general scanning arrangement for generating a high resolution image. The scanning arrangement includes multiple transmitter elements and multiple receiver elements that are positioned relative to an object.

FIG. 7 shows one embodiment, according to the present invention, of a general scanning arrangement for generating a high resolution image for detecting an object 104. The scanning arrangement includes an array of transmitter elements 106 and an array of receiver elements 108 that are positioned relative to the object 104. In one embodiment, the object 104 to be imaged through the high resolution imaging ability of the present invention, is a lesion which is part of the female breast 102. The breast 102 of a subject is suspended under gravity in a fluid-filled coupling chamber/enclosure 110 that has at least two directions of motion (i.e., can rotate and move vertically as shown by arrows 112 and 114) relative to the breast. The transmitting array elements 106 and receiving array elements 108 lie opposite to each other in precise alignment, whereby preferably a substantially orthogonally coded signal transmitted by each element in the transmitting array travels through the coupling enclosure, comprising the water bath and the breast. That portion of each of the substantially orthogonally coded signals which arrives first at the respective receiver element in the receiving array is recorded. This recording is done by defining a time window at the receiver that contains the early arriving signals, and then applying a detection threshold to capture the first arrival. The detection threshold is selected on the basis of the statistics of the data noise for a given probability of false detection. After detection of each of the first arriving signals, a data segment approximately equal to the transmitted signal length is extracted and analyzed to obtain the scattering information of interest (viz, attenuation and time-of-flight profiles of the signals) after data reduction involving the operation of the correlator-integrator structure 43, 53 and 63 in FIG. 4.

The benefits of the system according to the present invention include a high signal-to-noise ratio (SNR) and low cross-talk and multipath effects at the array of receiver elements due to the substantially orthogonal coded signals employed in its operation. This allows the system to recover scattering information from the transmitted signal that propagates through the object and within the fluid filled enclosure 110.

A straight-line path of propagation for the transmitted signal is implicitly assumed for creating the tomographic image using the processing discussed above for the first arrival portions of the transmitted signal. However, in reality a straight line path of the transmitted signal is not necessarily achieved due to the signals undergoing refraction and diffraction effects. The refraction effects can be subsequently corrected for, by iterative procedures such as algebraic reconstruction techniques as is known to one skilled in the art. The effects of diffraction are mitigated through innovative signal processing methods. One method to mitigate the effects of diffraction are described in applicant's co-pending application for patent, Ser. No. 10/117,468, filed Apr. 5, 2002, the contents of which are incorporated herein by reference. (This co-pending application claims priority to provisional application Ser. No. 60/282,002, filed Apr. 6, 2001.

The enclosure 110 housing the arrays rotates and elevates to take several angular and vertical scanning positions in order to scan the entire 3D volume of interest, preferably in a helical scan pattern. In one embodiment, the horizontal (azimuthal) dimension of the scanned object is covered by the length of the array. The angular and vertical scanning is repeated for a large number of different angles covering 360°. For instance, two 512×8 arrays with 0.5 mm pitch (i.e., inter-element distance from start of one to start of the next) will require 512 angular and 40 vertical scan positions of the transmitter/receiver array to cover a cylindrical volume of interest having a diameter of 20 cm and a length of 16 cm. In each scan position, the array elements fire and record in a specified order (for instance, simultaneously) following control commands by the host computer. Typically, a large number of transmitting elements (e.g., 64 in the example cited) fire simultaneously according to a specified set of substantially orthogonal coded waveforms (e.g., pseudorandom pulse sequences) in order to reduce scanning time at a given scan position. Cross-talk problems are minimized by cross-correlating the received signals at the corresponding receiver elements with the respective orthogonal code (akin to code-division-multiple-access communication schemes). In addition, cross-correlation at the receiver may enhance the output SNR and improve the accuracy of the scattering information which includes attenuation and time-of-flight profiles.

Each horizontal scanning line yields attenuation and time-of-flight profiles of ultrasonic transmission values. All profiles of each type collected from the various angles for a specific horizontal plane form the sinogram, which yields a 2D image for the respective horizontal plane/slice after inverse Radon transform or filtered back projection processing (one image for each type of profile). The latter are widely used and known to one skilled in the art. The stack of these 2D slices is used to form a 3D image of the object of interest, after appropriate image processing. One such image processing method is described in the provisional application "Multi-mode processing for ultrasonic imaging" having Ser. No. 60/362,568, filed Mar. 6, 2002. Image analysis may also provide a diagnostic advisory based on statistical inference with regard to features of interest in the image. The 3D image may be displayed with an advisory indicating the presence or absence of the object of interest on a computer screen.

Figure 8:
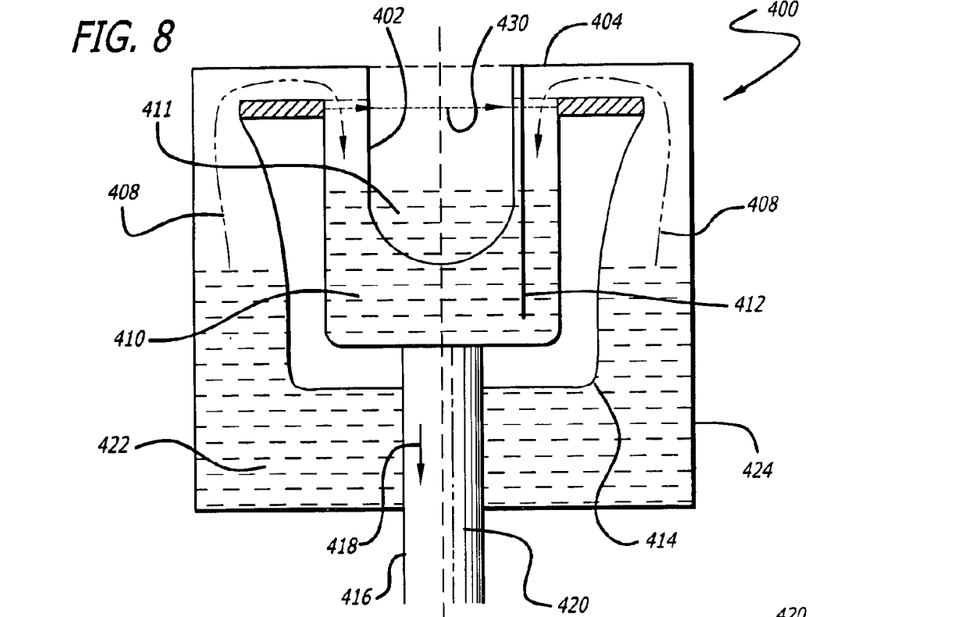
FIG. 8 shows one embodiment, according to the present invention, of a system used in the creation of a high resolution image of an object that is fixed relative to a frame of reference.
Figures 9, 10:
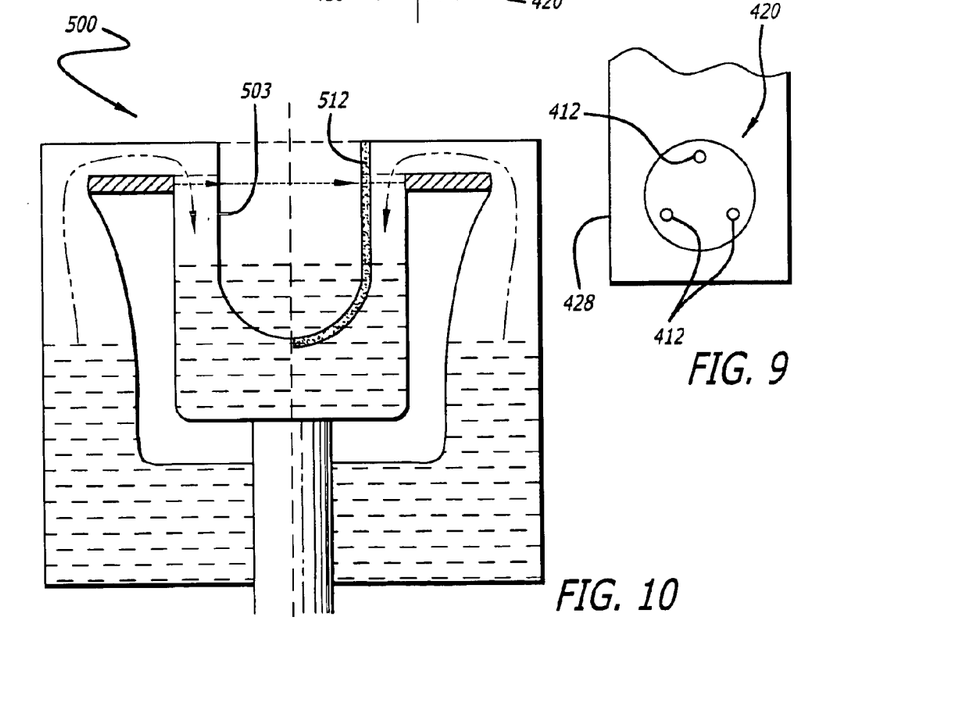
FIG. 9 shows a top view of the system in FIG. 8.
FIG. 10 shows another embodiment, according to the present invention, of a system used in the creation of a high resolution image of an object that is fixed relative to a frame of reference.

FIG. 8 and FIG. 9 show one embodiment, according to the present invention, of a system 400 for creating a high resolution image of an object that is fixed relative to a frame of reference. The system employs an acoustically transparent receptacle 402 that is used to hold the scanned breast in a liquid bath 410 so that (i) inadvertent motion of the breast (not shown) is minimized during scanning, (ii) acoustic coupling between breast (not shown) and transducers is optimized, (iii) a fixed co-ordinate system due to the presence of indicia or locator wires 412 is provided for 3D imaging, (iv) sanitation of fluid 410 is secured by the containment of fluid 411 in the receptacle. Circulation of the fluid 422 from the stationary chamber 424 into the rotating chamber 414 is achieved via the path depicted by arrows 408.

The space between the transducer rotating chamber/enclosure 414 and the breast receptacle 402 is filled with an acoustic coupling fluid 410 that optimizes the relation between acoustic coupling and forces exerted on the receptacle due to rotating motion of the fluid 410. Fluid 410 is filled in the rotating chamber 414 automatically, during elevation changes when scanning, using the pool of liquid 422 in the outer stationary chamber 424. The fill path of the fluid 422 between the two chambers is shown by arrows 408. The rotation and elevation changes associated with the chamber 414 is provided by shaft 416.

In one embodiment, fixed reference of imaging co-ordinates is provided by at least one thin and acoustically opaque vertical wire 412 that is affixed on the top of the stationary chamber 424 at a fixed location. In another embodiment there are three such wires surrounding the receptacle. Each wire 412 intersects a coronal imaging plane 430 (2D tomogram) at one point thereby yielding a fixed reference of imaging co-ordinates. In another embodiment, the three intersection or "locator" points, corresponding to the three wires, in each 2D slice serve also as reference points (beacons) for correcting any possible motion errors in the 2D sinogram of each tomogram by means of focusing processing algorithms. In another embodiment, at least one tape 512 may be affixed to the receptacle 503 to provide a fixed reference of imaging co-ordinates as shown in FIG. 10.

Having described the invention in detail, those skilled in the art will appreciate that, given the present disclosure, modifications may be made to the invention without departing from the spirit of the inventive concept described herein. Therefore, it is not intended that the scope of the invention be limited to the specific and preferred embodiments illustrated and described. Rather, it is intended that the scope of the invention be determined by the appended claims.

I claim the following:

1. A system for creating an image of an object comprising:
    a) at least one transmitter that transmits a signal;
    b) at least one receiver positioned to receive the signal;
    c) said at least one transmitter including a transducer that has at least two linear dimensions that are no greater than one millimeter;
    d) an area between said transmitter and said receiver for receiving the object in a position that causes at least portions of the signal to scatter before the signal is received by said receiver;
    e) a processor in communication with said receiver for extracting scattering information from the signal and for creating an image of the object based on the scattering information; and
    f) wherein said at least one transmitter and said at least one receiver are operable in transmission mode.

2. The system of claim 1 further including a housing apparatus that fixes said transmitter and said receiver relative to one another and that allows said transmitter and said receiver to move relative to the object.

3. The system of claim 2 wherein said housing apparatus allows said transmitter and said receiver to move relative to the object in at least two different directions.

4. The system of claim 1 further including a housing apparatus that fixes said transmitter and said receiver relative to one another and that allows said transmitter and said receiver to move relative to the object.

5. The system of claim 1 wherein the scattering information includes an attenuation profile and a time of flight profile of the signal.

6. The system of claim 1 wherein said at least one transmitter and said at least one receiver are affixed on a surface of an enclosure.

7. The system of claim 6 wherein the enclosure is configured to hold a fluid.

8. The system of claim 1 wherein the signal transmitted by said at least one transmitter is an ultrasonic signal.

9. The system of claim 1 wherein said at least one receiver includes a transducer having no linear dimension greater than one millimeter.

10. A system for creating an image of an object that has at least one linear dimension of less than one millimeter comprising:
    a) at least one transmitter that transmits a signal;
    b) at least one receiver positioned to receive the signal;
    c) an area between said transmitter and said receiver for receiving the object in a position that causes at least portions of the signal to be scattered before the signal is received by said receiver;

d) a processor in communication with said receiver for creating a discernable image of the dimension of the object that is less than one millimeter;

e) wherein the at least one transmitter has at least two linear dimensions that are no greater than one millimeter; and f) wherein the at least one transmitter and the at least one receiver are operable in transmission mode.

11. The system of claim 10 further including a housing apparatus that fixes said transmitter and said receiver relative to one another and that allows said transmitter and said receiver to move relative to the object.

12. The system of claim 11 wherein said housing apparatus allows said transmitter and said receiver to move relative to the object in at least two different directions.

13. The system of claim 10 wherein said at least one transmitter and said at least one receiver are affixed on a surface of an enclosure.

14. The system of claim 13 wherein the enclosure is configured to hold a fluid.

15. The system of claim 10 wherein the signal transmitted by the at least one transmitter is an ultrasonic signal.

16. The system of claim 10 wherein the processor includes a system for extracting an attenuation profile and a time of flight profile from the signal and for creating the image of the object based on these profiles.

17. The system of claim 10 wherein said at least one receiver includes a transducer having no linear dimension greater than one millimeter.

18. A method for creating an image of object positioned in an area between a transmitter and a receiver comprising:

a) transmitting a signal from at least one transmitter;

b) receiving a signal through at least one receiver;

c) the at least one transmitter including a transducer that has at least two linear dimensions that are no greater than one millimeter;

d) extracting scattering information from the received signal;

e) creating an image of the object based on the scattering information; and f) wherein said at least one transmitter and said at least one receiver are operable in transmission mode.

19. The method of claim 18 further comprising moving said transmitter and said receiver relative to the object.

20. The method of claim 19 wherein the moving is in at least two different directions.

21. The system of claim 18 wherein the scattering information includes an attenuation profile and a time of flight profile of the signal.

22. The method of claim 18 wherein said at least one transmitter and said at least one receiver are affixed on a surface of an enclosure.

23. The method of claim 22 wherein the enclosure is configured to hold a fluid.

24. The method of claim 18 wherein the signal transmitted by said at least one transmitter is an ultrasonic signal.

25. The method of claim 18 wherein said at least one receiver includes a transducer having no linear dimension greater than one millimeter.

26. A system for creating an image of an object comprising:

a) at least one transmitter that transmits a signal;

b) at least one receiver positioned to receive the signal;

c) an area between said transmitter and said receiver for receiving the object in a position that causes at least portions of the signal to be scattered before the signal is received by said receiver;

d) a processor in communication with said receiver for creating an image of the object;

e) wherein said at least one transmitter includes a transducer having at least two linear dimensions that are no greater than one millimeter; and f) wherein said at least one transmitter and said at least one receiver are operable in transmission mode.

27. The method of claim 26 wherein said at least one receiver includes a transducer having no linear dimension greater than one millimeter.

28. A system for creating an image of an object comprising:

a) at least one transmitter that transmits a signal;

b) at least one receiver positioned to receive the signal;

c) an area between said transmitter and said receiver for receiving the object in a position that causes at least portions of the signal to be altered before the signal is received by said receiver;

d) a processor in communication with said receiver for creating an image of the object;

e) wherein said at least one transmitter includes a transducer having at least two linear dimensions that are no greater than one millimeter; and f) wherein said at least one transmitter and said at least one receiver are operable in transmission mode.

29. The system of claim 28 wherein the at least portions of the signal are altered through scattering by the object.

30. The system of claim 28 wherein said at least one receiver includes a transducer having no linear dimension greater than one millimeter.

* * * * *